United States Patent
Nageri

(10) Patent No.: US 10,603,485 B2
(45) Date of Patent: Mar. 31, 2020

(54) FEATURES IN INCREASED SURFACE AREA ON NEUROMODULATION LEADS

(71) Applicant: Boston Scientific Neuromodulation Corporation, Valencia, CA (US)

(72) Inventor: Ranjan Krishna Mukhari Nageri, Valencia, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 282 days.

(21) Appl. No.: 15/819,612

(22) Filed: Nov. 21, 2017

(65) Prior Publication Data

US 2018/0147407 A1    May 31, 2018

Related U.S. Application Data

(60) Provisional application No. 62/427,095, filed on Nov. 28, 2016.

(51) Int. Cl.
| | | |
|---|---|---|
| *A61N 1/05* | (2006.01) | |
| *A61N 1/372* | (2006.01) | |
| *A61N 1/378* | (2006.01) | |

(52) U.S. Cl.
CPC .......... *A61N 1/0551* (2013.01); *A61N 1/3787* (2013.01); *A61N 1/37264* (2013.01)

(58) Field of Classification Search
CPC .. A61N 1/0551; A61N 1/0553; A61N 1/3787; A61N 1/37264
See application file for complete search history.

(56) References Cited

U.S. PATENT DOCUMENTS

| | | |
|---|---|---|
| 4,677,989 A | 7/1987 | Robblee |
| 5,683,443 A | 11/1997 | Munshi et al. |
| 6,181,969 B1 | 1/2001 | Gord |
| 6,253,110 B1 | 6/2001 | Brabec et al. |
| 6,516,227 B1 | 2/2003 | Meadows et al. |

(Continued)

OTHER PUBLICATIONS

M. Sessolo, D. Khodagholy, J. Rinvay, F. Maddalena, M. Gleyzes, E. Steidl, B. Buisson, and G. G. Malliaras, "Easy-to-Fabricate Conducting Polymer Microelectrode Arrays," Adv. Mater., 25 (2013) 2135-2139.

(Continued)

*Primary Examiner* — Alyssa M Alter
(74) *Attorney, Agent, or Firm* — Lowe Graham Jones PLLC; Bruce E. Black

(57) ABSTRACT

A stimulation lead includes a lead body; terminals disposed along the proximal end portion of the lead body; electrodes disposed along the distal end portion of the lead body, the electrodes including segmented electrodes. Each of the segmented electrodes includes a base and at least one finned arrangement radially extending from the base. Each of the finned arrangement includes elongated segments, each of the elongated segments extending along at least 50% of a length of a dimension of the base. Each finned arrangement also includes curved segments, where a first curved segment connects a first end portion of a first elongated segment to a first end portion of an intermediate elongated segment and a second curved segment connects a second end portion of a second elongated segment to a second end portion of an intermediate elongated segment. The lead also includes conductors electrically coupling the terminals to the electrodes.

20 Claims, 12 Drawing Sheets

(56) References Cited

U.S. PATENT DOCUMENTS

| | | |
|---|---|---|
| 6,555,157 B1 | 4/2003 | Hossainy |
| 6,609,029 B1 | 8/2003 | Mann et al. |
| 6,609,032 B1 | 8/2003 | Woods et al. |
| 6,669,980 B2 | 12/2003 | Hansen |
| 6,741,892 B1 | 5/2004 | Meadows et al. |
| 7,037,332 B2 | 5/2006 | Kutryk et al. |
| 7,244,150 B1 | 7/2007 | Brase et al. |
| 7,329,366 B1 | 2/2008 | Gale et al. |
| 7,437,193 B2 | 10/2008 | Parramon et al. |
| 7,450,997 B1 | 11/2008 | Pianca et al. |
| 7,491,233 B1 | 2/2009 | Ding et al. |
| 7,591,841 B2 | 9/2009 | Hossainy et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,803,021 B1 | 9/2010 | Brase |
| 7,809,446 B2 | 10/2010 | Meadows et al. |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,322,026 B2 | 12/2012 | McDonald |
| 8,364,278 B2 | 1/2013 | Pianca et al. |
| 8,391,985 B2 | 3/2013 | McDonald |
| 8,483,237 B2 | 7/2013 | Zimmerman et al. |
| 8,688,234 B2 | 4/2014 | Pianca et al. |
| 8,688,235 B1 | 4/2014 | Pianca et al. |
| 8,831,742 B2 | 9/2014 | Pianca et al. |
| 8,942,810 B2 | 1/2015 | DiGiore et al. |
| 2005/0288722 A1 | 12/2005 | Eigler et al. |
| 2007/0150036 A1 | 6/2007 | Anderson |
| 2008/0071320 A1 | 3/2008 | Brase |
| 2009/0276021 A1 | 11/2009 | Meadows et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0118815 A1 | 5/2011 | Kuzma et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0237605 A1 | 9/2012 | Messersmith et al. |
| 2012/0316615 A1 | 12/2012 | DiGiore et al. |
| 2013/0105071 A1 | 5/2013 | DiGiore et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0274843 A1 | 10/2013 | Barker et al. |
| 2013/0274844 A1 | 10/2013 | Leven et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0142670 A1 | 5/2014 | Radhakrishnan et al. |
| 2014/0277311 A1 | 9/2014 | Victorine et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |
| 2015/0224310 A1 | 8/2015 | Sharma et al. |
| 2016/0038743 A1 | 2/2016 | Foster et al. |
| 2016/0228692 A1 | 8/2016 | Steinke et al. |
| 2016/0375237 A1 | 12/2016 | Hahn et al. |

OTHER PUBLICATIONS

X. Ding, C. Yang, T.P. Lim, L.Y. Hsu, A.C. Engler, J.L. Hedrick, Y.-Y. Yang, Antibacterial and antifouling catheter coatings using surface grafted PEG-b-cationic polycarbonate diblock copolymers, Biomaterials, 33 (2012) 6593-6603.

M. Li, K.G. Neoh, L.Q. Xu, R. Wang, E.-T. Kang, T. Lau, D.P. Olszyna, E. Chiong, Surface modification of silicone for biomedical applications requiring long-term antibacterial, antifouling, and hemocompatible properties, Langmuir, 28 (2012) 16408-16422.

Axel Blau (2011). Prospects for Neuroprosthetics: Flexible Microelectrode Arrays with Polymer Conductors, Applied Biomedical Engineering, Dr. Gaetano Gargiulo (Ed.), ISBN: 978-953-307-256-2, InTech, Available from: http://www.intechopen.com/books/applied-biomedical-engineering/prospects-for-neuroprostheticsflexiblemicroelectrode-arrays-with-polymer-conductors.

X. Khoo, P. Hamilton, G.A. O'Toole, B.D. Snyder, D.J. Kenan, M.W. Grinstaff, Directed assembly of PEGylated-peptide coatings for infection-resistant titanium metal, J. Am. Chem. Soc., 131 (2009) 10992-10997.

K.D. Park, Y.S. Kim, D.K. Kim, Y.H. Kim, E.H.B. Lee, H. Suh, K.S. Choi, Bacterial adhesion on PEG modified polyurethane surfaces, Biomaterials, 19 (1998) 851-859.

FEATURES IN INCREASED SURFACE AREA ON NEUROMODULATION LEADS

CROSS-REFERENCE TO RELATED APPLICATIONS

This application claims the benefit under 35 U.S.C. § 119(e) of U.S. Provisional Patent Application Ser. No. 62/427,095, filed Nov. 28, 2016, which is incorporated herein by reference.

FIELD

The present invention is directed to the area of implantable electrical stimulation systems and methods of making and using the systems. The present invention is also directed to electrical stimulation leads, systems, and methods for stimulation of body tissues.

BACKGROUND

Implantable electrical stimulation systems have proven therapeutic in a variety of diseases and disorders. For example, spinal cord stimulation systems have been used as a therapeutic modality for the treatment of chronic pain syndromes. Sacral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a stimulation lead that includes a lead body having a longitudinal surface, a distal end portion, a proximal end portion, and a longitudinal length; terminals disposed along the proximal end portion of the lead body; electrodes disposed along the distal end portion of the lead body, the electrodes including segmented electrodes. Each of the segmented electrodes includes a base and at least one finned arrangement radially extending from the base. The base includes a perimeter around the base and the at least one finned arrangement is spaced apart from the perimeter. Each of the at least one finned arrangement includes elongated segments including a first elongated segment, a second elongated segment, and at least one intermediate elongated segment disposed between the first and second elongated segments, each of the elongated segments extending along at least 50% of a length of a dimension of the base and having a first end portion and a second end portion. Each of the at least one finned arrangement also includes curved segments including a first curved segment and a second curved segment, where the first curved segment connects the first end portion of the first elongated segment to the first end portion of at least one of the at least one intermediate elongated segment that is adjacent to the first elongated segment and the second curved segment connects the second end portion of the second elongated segment to the second end portion of one of the at least one intermediate elongated segment that is adjacent to the second elongated segment. The lead also includes conductors electrically coupling the terminals to the electrodes.

In at least some embodiments, each of the elongated segments extends along at least 75% of the length of the dimension of the base. In at least some embodiments, each of the curved segments defines a turn of at least 150°. In at least some embodiments, all of the elongated segments are parallel to each other.

In at least some embodiments, the at least one finned arrangement includes multiple finned arrangements that are spaced apart from each other along an axis of the base. In at least some embodiments, the at least one intermediate elongated segment includes a single intermediate elongated segment. In at least some embodiments, the at least one intermediate elongated segment includes at least two intermediate segments connected together using at least one of the curved segments. In at least some embodiments, the at least one finned arrangement includes a single finned arrangement with at least 15 intermediate elongated segments.

In at least some embodiments, each of the elongated segments has a height of at least 0.0005 inches or 0.013 mm. In at least some embodiments, each of the elongated segments has a height of at least 0.0015 inches or 0.038 mm.

In at least some embodiments, the elongated segments are arranged such that a distance between a first elongated segment and a second elongated segment adjacent to the first elongated segment is no more than a height of the first elongated segment.

In at least some embodiments, each of the segmented electrodes has a first half and a second half. Each of the elongated segments of the at least one finned arrangement of the segmented electrode is disposed with the first end portions on the first half of the segmented electrode and with the second end portions on the second half of the segmented electrode.

Another embodiment is an electrical stimulation system that includes any of the stimulation leads described above; and a control module coupleable to the lead. The control module includes a housing; and an electronic subassembly disposed in the housing.

A further embodiment is a segmented stimulation electrode that includes a base having a perimeter around the base; and at least one finned arrangement radially extending from the base. The at least one finned arrangement is spaced apart from the perimeter. Each of the at least one finned arrangement includes elongated segments including a first elongated segment, a second elongated segment, and at least one intermediate elongated segment disposed between the first and second elongated segments. Each of the elongated segments extends along at least 50% of a length of a dimension of the base and has a first end portion and a second end portion. Each of the at least one finned arrangement also includes curved segments. The curved segments include a first curved segment and a second curved segment. The first curved segment connects the first end portion of the first elongated segment to the first end portion of at least one of the at least one intermediate elongated segment that is adjacent to the first elongated segment. The second curved segment connects the second end portion of the second elongated segment to the second end portion of one of the at least one intermediate elongated segment that is adjacent to the second elongated segment.

In at least some embodiments, each of the elongated segments extends along at least 75% of the length of the dimension of the base. In at least some embodiments, each of the curved segments defines a turn of at least 150°. In at least some embodiments, the at least one intermediate elongated segment includes a single intermediate elongated segment.

Another embodiment is a method of making a segmented stimulation electrode, the method includes providing a base having a perimeter around the base; and forming at least one finned arrangement radially extending from the base. The at least one finned arrangement is spaced apart from the perimeter. Each of the at least one finned arrangement includes elongated segments including a first elongated segment, a second elongated segment, and at least one intermediate elongated segment disposed between the first and second elongated segments. Each of the elongated segments extends along at least 50% of a length of a dimension of the base and having a first end portion and a second end portion. Each of the at least one finned arrangement also includes curved segments including a first curved segment and a second curved segment. The first curved segment connects the first end portion of the first elongated segment to the first end portion of at least one of the at least one intermediate elongated segment that is adjacent to the first elongated segment. The second curved segment connects the second end portion of the second elongated segment to the second end portion of one of the at least one intermediate elongated segment that is adjacent to the second elongated segment.

In at least some embodiments, forming the at least one finned arrangement includes building at least one portion of the at least one finned arrangement up from the base.

In at least some embodiments, forming the at least one finned arrangement includes removing at least one portion of the base.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to electrical stimulation leads, systems, and methods for stimulation of body tissues.

Suitable implantable electrical stimulation systems include, but are not limited to, an electrode lead ("lead") with one or more electrodes disposed on a distal end portion of the lead and one or more terminals disposed on one or more proximal end portions of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/

0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Figure 1A:
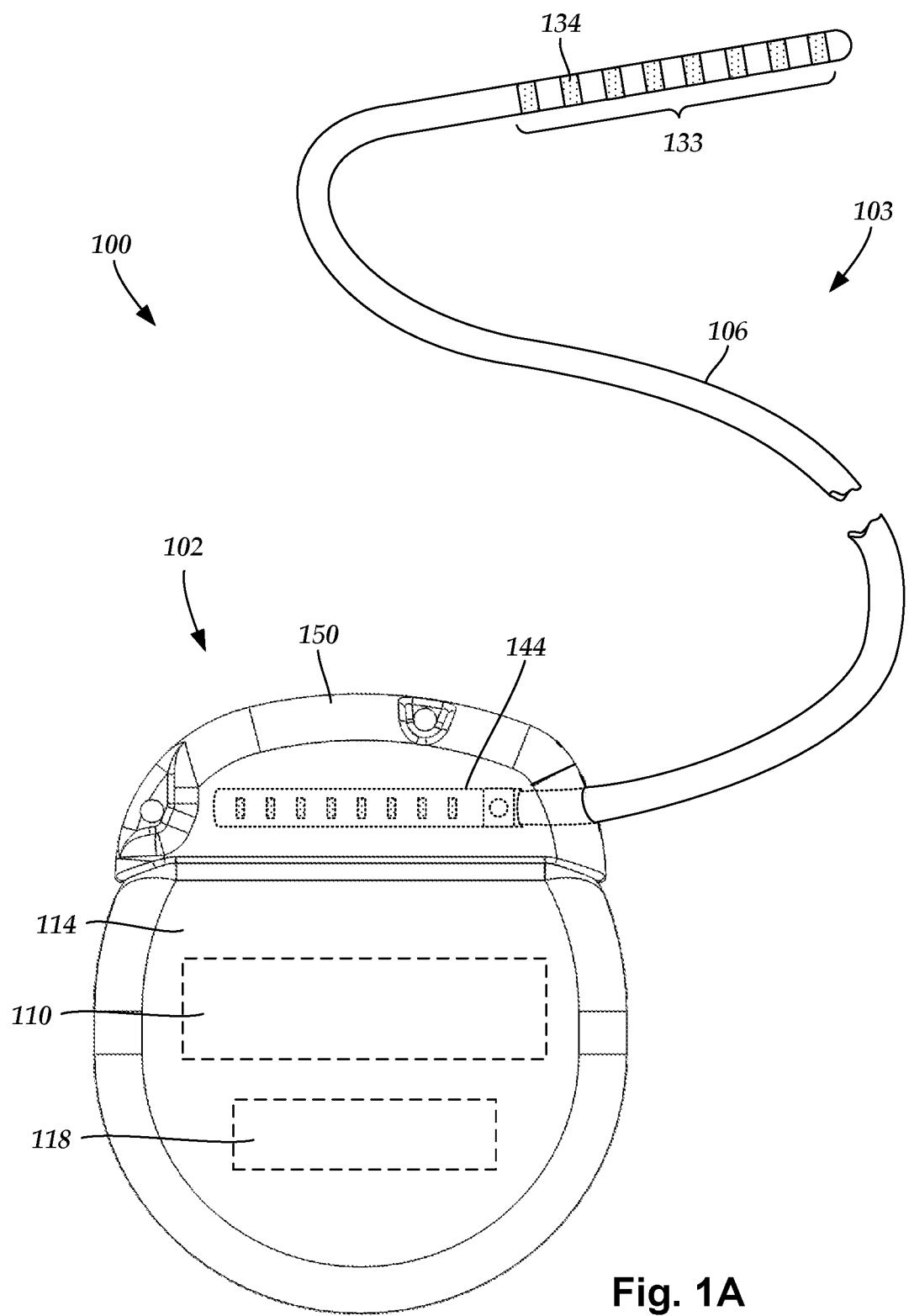
FIG. 1A is a schematic view of some embodiments of an electrical stimulation system that includes a percutaneous lead body coupled to a control module, according to the invention.

FIG. 1A schematically illustrates some embodiments of an electrical stimulation system 100. The electrical stimulation system 100 includes a control module (for example, a stimulator or pulse generator) 102 and a percutaneous lead 103. The lead 103 includes multiple electrodes 134 that form an array of electrodes 133. The control module 102 typically includes an electronic subassembly 110 and an optional power source 118 disposed in a sealed housing 114. The lead 103 includes a lead body 106 coupling the control module 102 to the plurality of electrodes 134. In at least some embodiments, the lead body 106 is isodiametric.

The control module 102 typically includes one or more connector assemblies 144 into which the proximal end portion of the lead body 106 can be plugged to make an electrical connection via connector contacts (for example, 216 in FIG. 2A) disposed in the connector assembly 144 and terminals (for example, 210 in FIG. 2A) disposed along the lead body 106. The connector contacts are coupled to the electronic subassembly 110 and the terminals are coupled to the electrodes 134. Optionally, the control module 102 may include a plurality of connector assemblies 144.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions (not shown) can be disposed between the lead body 106 and the control module 102 to extend the distance between the lead body 106 and the control module 102.

The electrical stimulation system or components of the electrical stimulation system, including the lead body 106 and the control module 102, are typically implanted into the body of a patient. The electrical stimulation system 100 can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of the following materials: platinum, platinum iridium, palladium, or titanium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1A, eight electrodes 134 are shown. The electrodes 134 can be formed in any suitable shape including, for example, round, oval, triangular, rectangular, pentagonal, hexagonal, heptagonal, octagonal, or the like. In the illustrated lead 103, the electrodes 134 are ring electrodes. Any number of ring electrodes can be disposed along the length of the lead body including, for example, one, two three, four, five, six, seven, eight, nine, ten, eleven, twelve, thirteen, fourteen, fifteen, sixteen or more ring electrodes. It will be understood that any number of ring electrodes can be disposed along the length of the lead body 106.

Figure 1B:
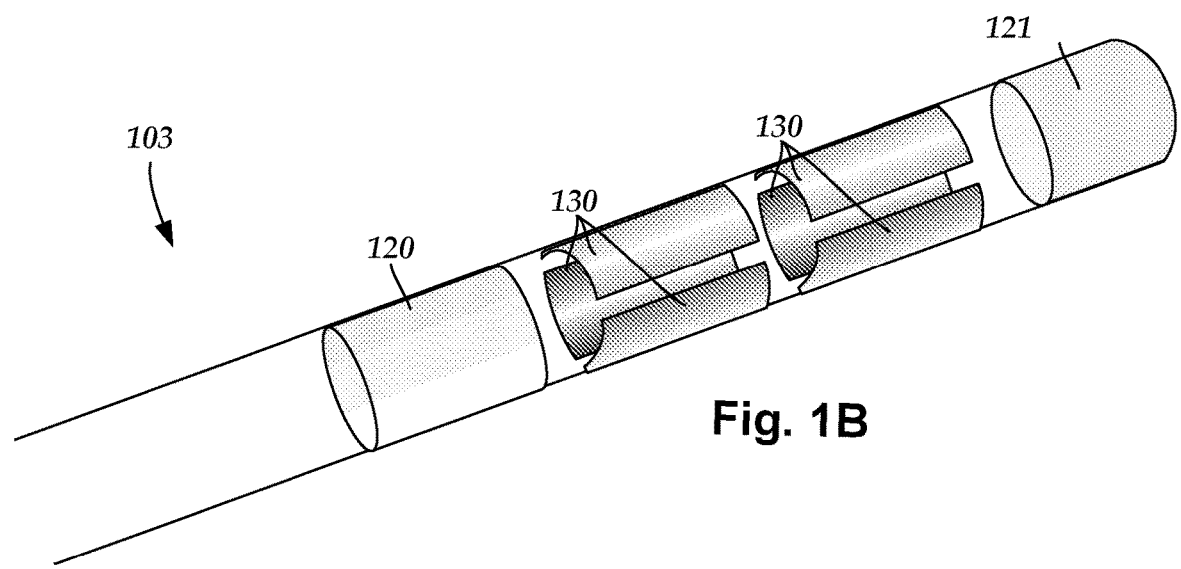
FIG. 1B is a schematic perspective view of some embodiments of a distal portion of the lead body of FIG. 1A, according to the invention.

FIG. 1B schematically illustrates a distal end portion of the lead 103 with a ring electrode 120, a tip electrode 121, and six segmented electrodes 130 in the distal electrode array 133. Segmented electrodes 130 may provide for superior current steering than ring electrodes 120 because target structures may not be disposed symmetrically about a longitudinal axis of the distal electrode array 133. Instead, a target may be located on one side of a plane running through the axis of the lead 103. Through the use of a radially segmented electrode array ("RSEA"), current steering can be performed not only along a length of the lead 103 but also around a circumference of the lead 103. This provides precise three-dimensional targeting and delivery of the current stimulus to target tissue, while potentially avoiding stimulation of other tissue. Examples of leads with segmented electrodes include U.S. Patent Applications Publication Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. Examples of leads with tip electrodes include at least some of the previously cited references, as well as U.S. Patent Applications Publication Nos. 2014/0296953 and 2014/0343647, all of which are incorporated herein by reference in their entireties. A lead with segmented electrodes may be a directional lead that can provide stimulation in a particular direction using the segmented electrodes.

Any number of segmented electrodes 130 may be disposed on the lead body 106 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 106. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes 130, where each set is disposed around a circumference of the lead 103 at a particular longitudinal portion of the lead 103. The lead 103 may have any number segmented electrodes 130 in a given set of segmented electrodes 130. The lead 103 may have one, two, three, four, five, six, seven, eight, or more segmented electrodes 130 in a given set. The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 103) may be identical in size and shape.

Each set of segmented electrodes 130 may be disposed around the circumference of the lead body 106 to form a substantially cylindrical shape around the lead body 106. The spacing between individual segmented electrodes 130 of a given set of the segmented electrodes 130 may be the same, or different from, the spacing between individual electrodes of another set of segmented electrodes 130 on the lead 103. In at least some embodiments, equal spaces, gaps or cutouts are disposed between each segmented electrode 130 around the circumference of the lead body 106. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 106.

Each electrode 134 in the array of electrodes 133 of the lead body 106 are typically disposed in, or separated by, a non-conductive, biocompatible material including, for example, silicone, polyurethane, and the like or combinations thereof. The lead body 106 may be formed in the desired shape by any process including, for example, extruding, molding (including injection molding), casting, and the like. Electrodes 134 and connecting wires can be disposed onto or within the lead body 106 either prior to or subsequent to a molding or casting process. The non-conductive material typically extends from the distal end portion of the lead body 106 to the proximal end portion of the lead body 106.

Terminals (for example, 210 in FIG. 2A) are typically disposed at the proximal end portion of the lead body 106 for connection to corresponding conductive contacts (for example, 216 in FIG. 2A) in one or more connector assemblies (for example, 144 in FIG. 1A) disposed on, for example, the control module 102 (or to other devices, such as conductive contacts on a lead extension, an operating room cable, a splitter, an adaptor, or the like).

Conductive wires extend from the plurality of terminals (see, for example, 210 in FIG. 2A) to the array of electrodes 133. Typically, each of the plurality of terminals is electrically coupled to at least one electrode 134 of the array of electrodes 133. In some embodiments, each of the plurality of terminals is coupled to a single electrode 134 of the array of electrodes 133.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end portion of the lead 103, for example, for inserting a stylet rod to facilitate placement of the lead 103 within a body of a patient. Additionally, there may also be one or more lumens (not shown) that open at, or near, the distal end portion of the lead 103, for example, for infusion of drugs or medication into the site of implantation of the lead 103. The one or more lumens may, optionally, be flushed continually, or on a regular basis, with saline or the like. The one or more lumens can be permanently or removably sealable at the distal end portion.

As discussed above, the lead body 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1A, the lead body 106 includes eight terminals that are shown coupled with eight conductive contacts disposed in the connector assembly 144.

Figure 2A:
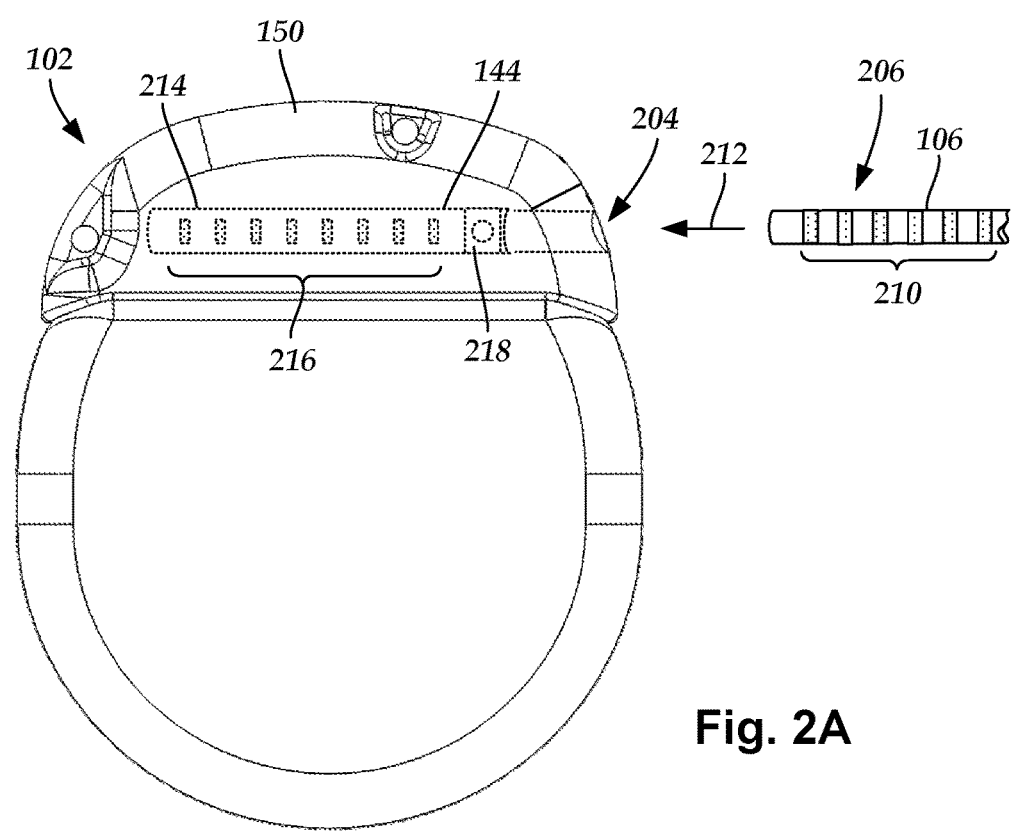
FIG. 2A is a schematic view of some embodiments of a plurality of connector assemblies disposed in the control module of FIG. 1A, the connector assemblies configured and arranged to receive proximal portions of the lead body of FIG. 1A, according to the invention.

FIG. 2A is a schematic view of some embodiments of a plurality of connector assemblies 144 disposed in the control module 102. In FIG. 2A, the proximal end portion 206 of the lead body 106 is shown configured and arranged for insertion to the control module 102.

In FIG. 2A, the connector assembly 144 is disposed in the header 150. In at least some embodiments, the header 150 defines a port 204 into which the proximal end portion 206 of the lead body 106 with terminals 210 can be inserted, as shown by directional arrow 212, in order to gain access to the connector contacts disposed in the connector assembly 144.

The connector assembly 144 includes a connector housing 214 and a plurality of connector contacts 216 disposed therein. Typically, the connector housing 214 defines a port (not shown) that provides access to the plurality of connector contacts 216. In at least some embodiments, the connector assembly 144 further includes a retaining element 218 configured and arranged to fasten the corresponding lead body 106 or lead retention sleeve to the connector assembly 144 when the lead body 106 is inserted into the connector assembly 144 to prevent undesired detachment of the lead body 106 from the connector assembly 144. For example, the retaining element 218 may include an aperture 220 (FIG. 2B) through which a fastener (for example, a set screw, pin, or the like) may be inserted and secured against an inserted lead body 106 or lead retention sleeve.

When the lead body 106 is inserted into the port 204, the connector contacts 216 can be aligned with the terminals 210 disposed on the lead body 106 to electrically couple the control module 102 to the electrodes (134 of FIG. 1A) disposed at the distal end portion of the lead body 106. Examples of connector assemblies in control modules are found in, for example, U.S. Pat. No. 7,244,150 and U.S. Patent Application Publication No. 2008/0071320, which are incorporated by reference.

Figure 2B:
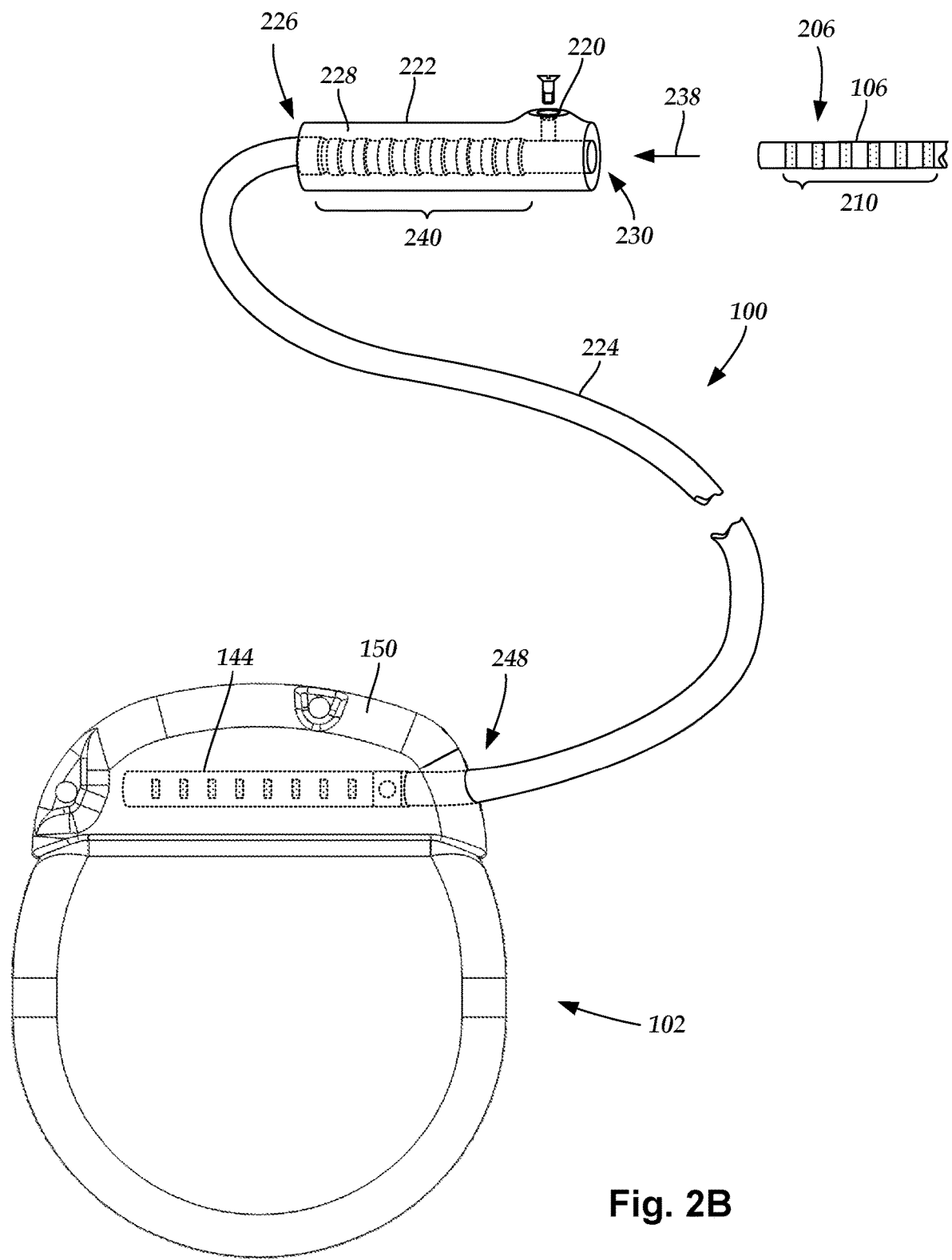
FIG. 2B is a schematic view of some embodiments of a proximal portion of the lead body of FIG. 1A, a lead extension, and the control module of FIG. 1A, the lead extension configured and arranged to couple the lead body to the control module, according to the invention.

In at least some embodiments, the electrical stimulation system 100 includes one or more lead extensions. The lead body 106 can be coupled to one or more lead extensions which, in turn, are coupled to the control module 102. In FIG. 2B, a lead extension connector assembly 222 is disposed on a lead extension 224. The lead extension connector assembly 222 is shown disposed at a distal end portion 226 of the lead extension 224. The lead extension connector assembly 222 includes a contact housing 228. The contact housing 228 defines at least one port 230 into which the proximal end portion 206 of the lead body 106 with terminals 210 can be inserted, as shown by directional arrow 238. The lead extension connector assembly 222 also includes a plurality of connector contacts 240. When the lead body 106 is inserted into the port 230, the connector contacts 240 disposed in the contact housing 228 can be aligned with the terminals 210 on the lead body 106 to electrically couple the lead extension 224 to the electrodes (134 of FIG. 1A) disposed at the distal end portion of the lead body 106.

The proximal end portion of a lead extension can be similarly configured and arranged as a proximal end portion of a lead body. The lead extension 224 may include a plurality of conductive wires (not shown) that electrically couple the connector contacts 240 to terminal on a proximal end portion 248 of the lead extension 224. The conductive wires disposed in the lead extension 224 can be electrically coupled to a plurality of terminals (not shown) disposed on the proximal end portion 248 of the lead extension 224. In at least some embodiments, the proximal end portion 248 of the lead extension 224 is configured and arranged for insertion into a lead extension connector assembly disposed in another lead extension. In other embodiments (as shown in FIG. 2B), the proximal end portion 248 of the lead extension 224 is configured and arranged for insertion into the connector assembly 144 disposed on the control module 102.

Figure 3A:
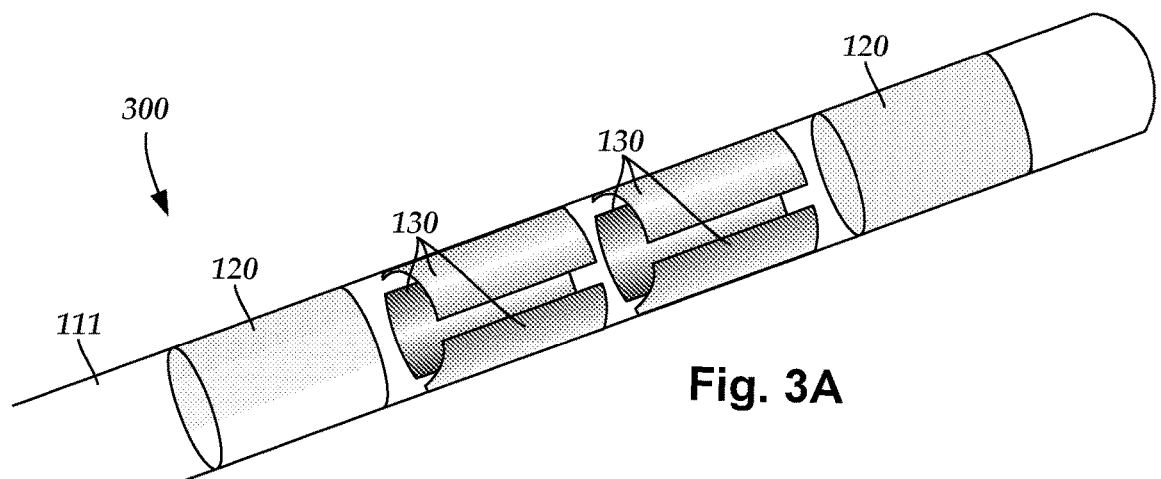
FIG. 3A is a schematic side view of some embodiments of a distal portion of an electrical stimulation lead, according to the invention.
Figure 3B:
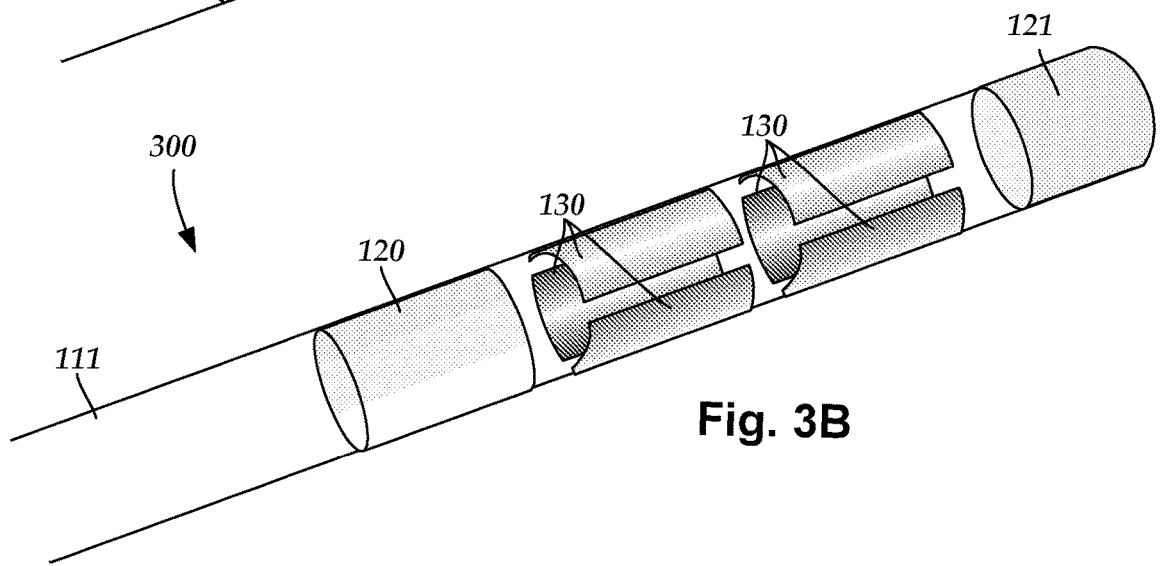
FIG. 3B is a schematic side view of a second embodiment of a distal portion of an electrical stimulation lead, according to the invention.
Figure 3C:
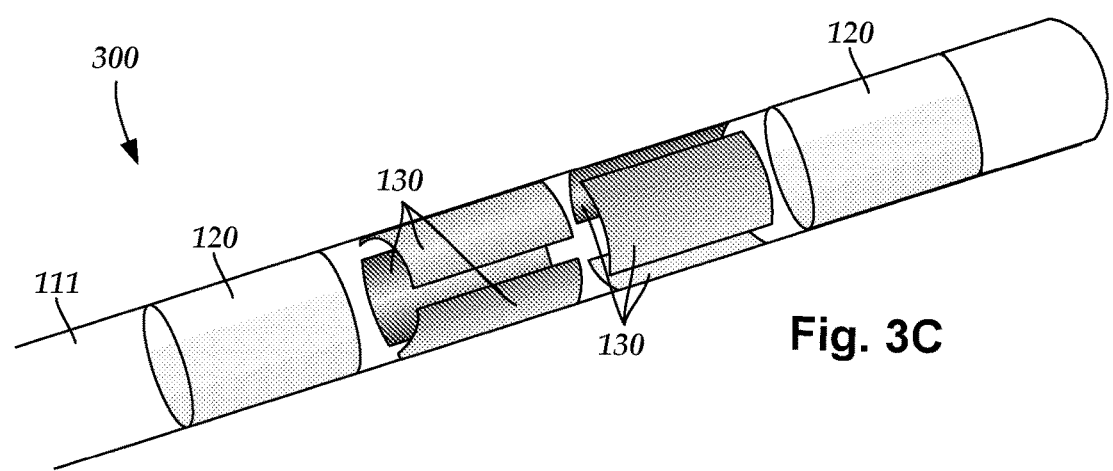
FIG. 3C is a schematic side view of a third embodiment of a distal portion of an electrical stimulation lead, according to the invention.
Figure 3D:
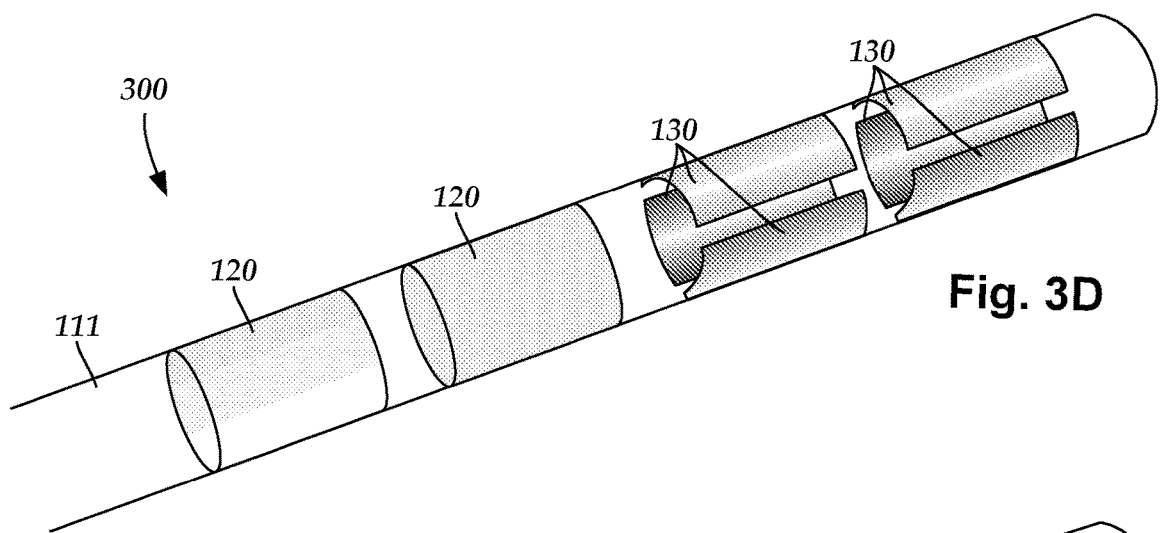
FIG. 3D is a schematic side view of a fourth embodiment of a distal portion of an electrical stimulation lead, according to the invention.
Figure 3E:
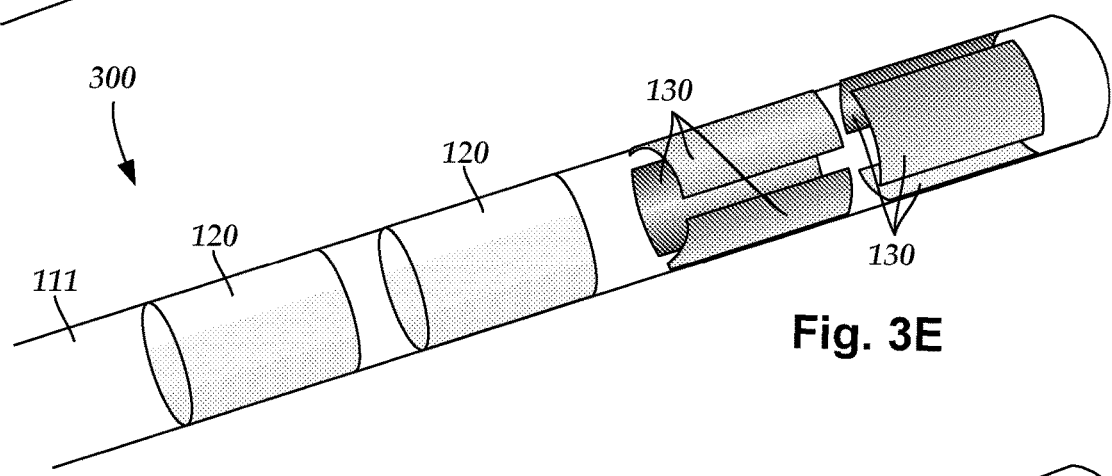
FIG. 3E is a schematic side view of a fifth embodiment of a distal portion of an electrical stimulation lead, according to the invention.
Figure 3F:
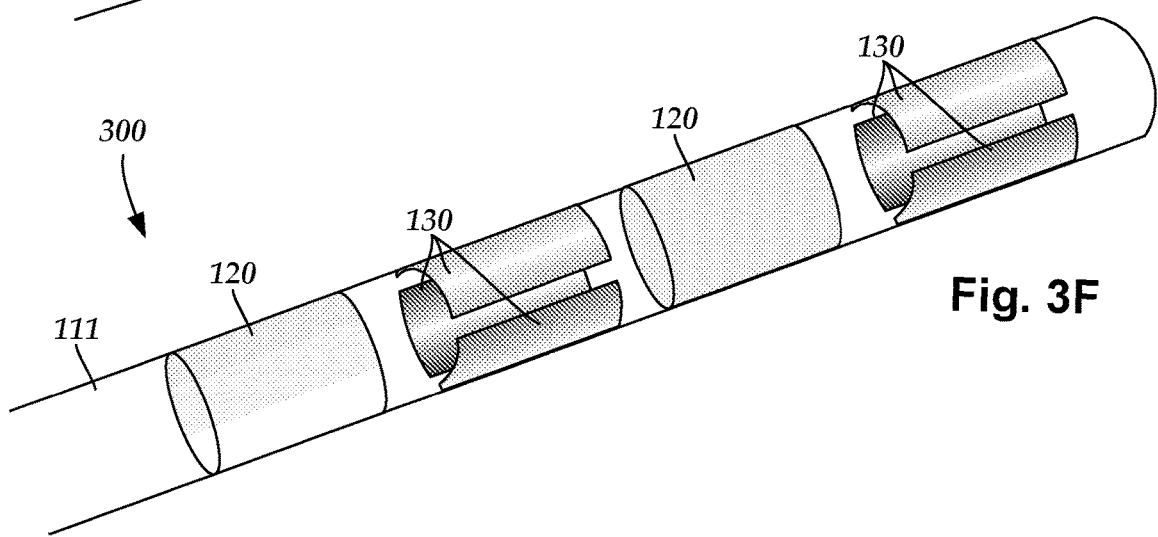
FIG. 3F is a schematic side view of a sixth embodiment of a distal portion of an electrical stimulation lead, according to the invention.
Figure 3G:
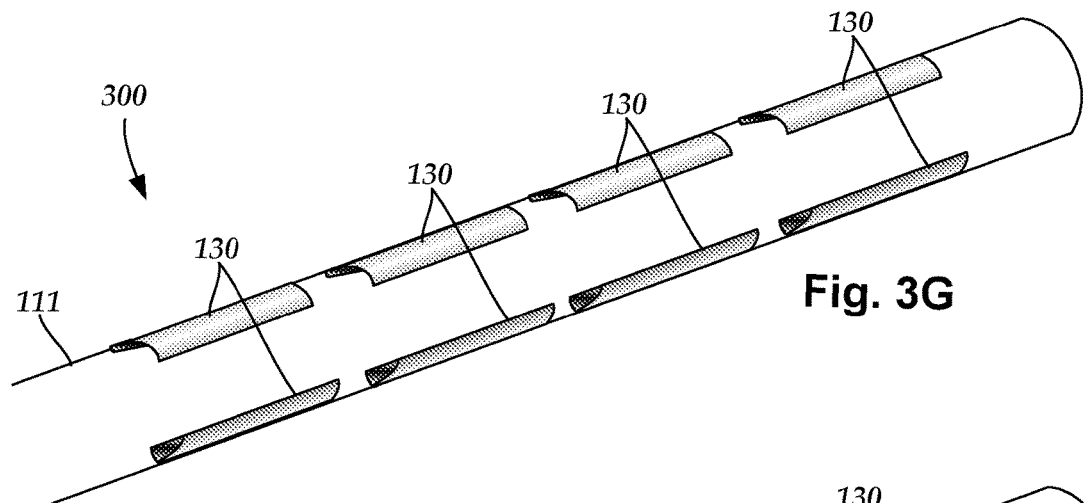
FIG. 3G is a schematic side view of a seventh embodiment of a distal portion of an electrical stimulation lead, according to the invention.
Figure 3H:
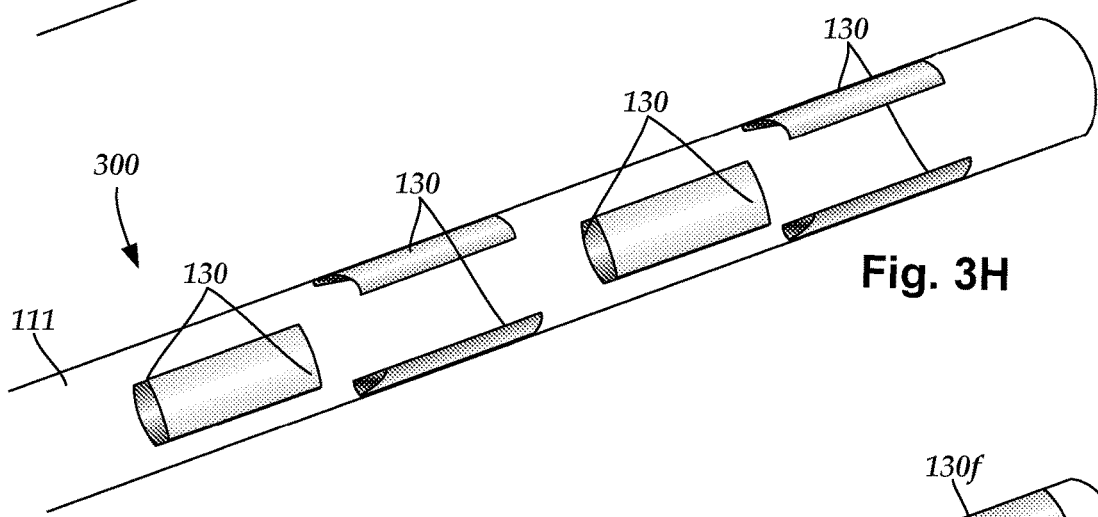
FIG. 3H is a schematic side view of an eighth embodiment of a distal portion of an electrical stimulation lead, according to the invention.

A lead can include ring electrodes, segmented electrodes, tip electrodes, or any other suitable electrode or any combination thereof. A lead containing ring electrodes and segmented electrodes may be arranged in any suitable configuration. FIG. 3A-3I illustrate a variety of different arrangements as non-limiting examples. The arrangements can include ring electrodes 120; segmented electrodes 130, 130a-130h; or tip electrodes 121 disposed along a lead body 111 of a lead 300. In at least some instances, arrangements of electrodes can be written in a shorthand, starting from the distal end portion, with each number indicating the number of electrodes at a particular longitudinal position. For example, the arrangement 1-3-3-1, illustrated in FIG. 3A, indicates a ring electrode 120 at the distal-most position, three segmented electrodes 130 at the next position, another three segmented electrodes 130 at the third position, and a ring 120 electrode at the proximal-most position. In addition, if there are multiple, sequential arrangements of the same type "x" can be used. As an example, the arrangement 3×5-1 (or 3×5+1) indicates five sets of three electrodes spaced apart longitudinally starting from the distal end portion with a single ring 120 electrode at the proximal-most position. Using this notation, the arrangements of the FIGS. 3A-3I can be written as follows: FIG. 3A: 1-3-3-1; FIG. 3B: 1-3-3-1; FIG. 3C: 1-3-3-1; FIG. 3D: 3-3-1-1; FIG. 3E: 3-3-1-1; FIG. 3F: 3-1-3-1; FIG. 3G: 2×4 (or 2-2-2-2); FIG. 3H: 2×4 (or 2-2-2-2); and FIG. 3I: 3×4-2×2 (or 3-3-3-3-2-2).

As non-limiting illustrations of electrode arrangements, when the lead 300 includes two ring electrodes 120 and two sets of segmented electrodes 130, the ring electrodes 120 can flank the two sets of segmented electrodes 130 (see, for example, FIGS. 1B, 3A, 3C). Alternately, the two ring electrodes 120 can be disposed proximal to the two sets of segmented electrodes 130 (see, for example, FIGS. 3D and 3E), or the two ring electrodes 120 can be disposed distal to the two sets of segmented electrodes 130 (not shown) or the two ring electrodes 120 and two sets of segmented electrodes 130 can alternate (see, for example, FIG. 3F). An arrangement may also include a tip electrode 121 (see, for example, FIG. 3B) or a single ring electrode 120 either proximal to, distal to, or between the segmented electrodes (not shown). In arrangements with more than two sets of segmented electrodes 130, the segmented electrodes 130 of the sets may be aligned (see, for example, FIGS. 3A, 3B, 3D, 3F, 3G, and 3I) or staggered (see, for example, FIGS. 3C, 3E, and 3H) relative to each other or in any other suitable relative arrangement. By varying the location of the segmented electrodes 130, different coverage of the target neurons may be selected. For example, the electrode arrangements of FIG. 3D or 3E may be useful if the physician anticipates that the neural target will be closer to a distal tip of the lead body 111. Any combination of ring electrodes 120, tip electrode 121, and segmented electrodes 130 may be disposed on the lead 300.

Figure 3I:
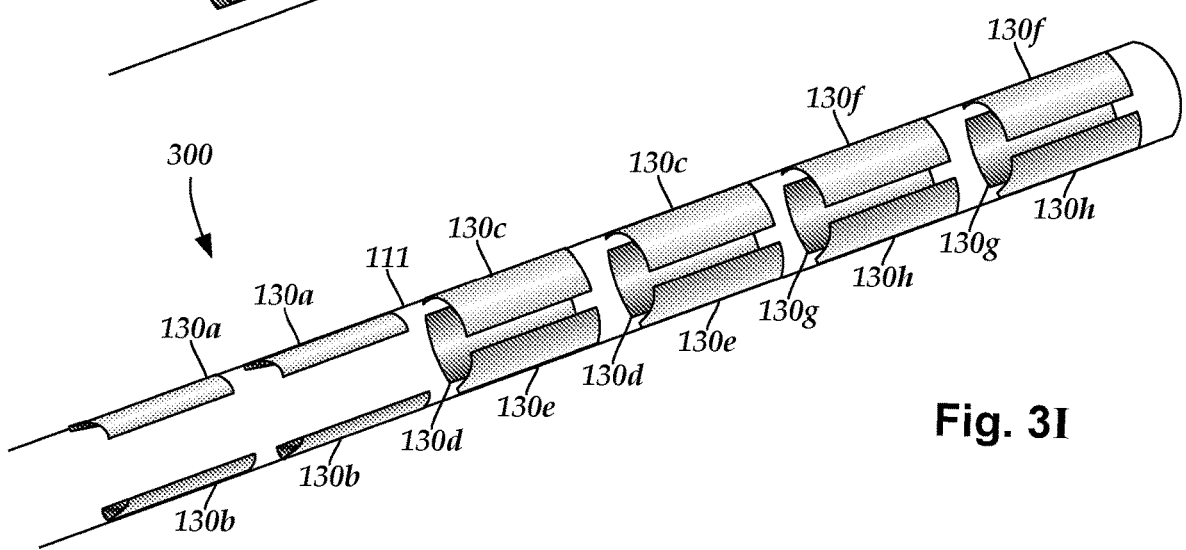
FIG. 3I is a schematic side view of a ninth embodiment of a distal portion of an electrical stimulation lead, according to the invention.

In some embodiments, the lead 300 may only include segmented electrodes 130. For example, FIGS. 3G and 3H illustrate the lead 300 with four pairs of segmented electrodes 130 (for example, a 2×4 arrangement) in aligned (FIG. 3G) or staggered configurations (FIG. 3H). Another arrangement has eight pairs of segmented electrodes 130 (for example, a 2×8 arrangement—not shown) in aligned or staggered configuration. FIG. 3I illustrates an arrangement in which different types of sets of segmented electrodes 130a-130h includes—in this case—four sets of three segmented electrodes 130c-130h and two pairs of segmented electrodes 130a, 130b (a 3×4-2×2 arrangement). Another example of a lead with segmented electrodes has the arrangement 3-3-2-3-2-3.

One variation of the arrangement of the lead 300 of FIG. 3I is to electrically gang (i.e., electrically short) segmented electrodes 130a-130h having the same reference numbers (for example, electrically gang the two segmented electrodes labeled 130a, etc.) Such electrical ganging can be accomplished in any suitable manner including by a conductor attached to two electrodes within the lead 100 or be electrically coupling the two electrodes to the same channel in the control module. Two, three, or more electrodes can be ganged together. The ganged electrodes provide longer virtual electrodes. In at least some embodiments, the ganged electrodes have an advantage, over very long individual contacts, of maintaining array flexibility while creating a longer virtual electrode. The ganged configuration maintains directionality and array span. Any other arrangement, including any of the arrangements illustrated in FIGS. 3A-3H, can include two or more sets of electrically ganged electrodes. In at least some embodiments, a lead can include electrodes that are electrically ganged and other electrodes that are not ganged together.

In at least some embodiments, one or more electrodes include surface features to increase surface area of the electrodes. Examples of such surface features include dimples, scores, cuts, trenches, grooves, channels, knurls, or other depressions or roughening of the surface.

Figure 4A:
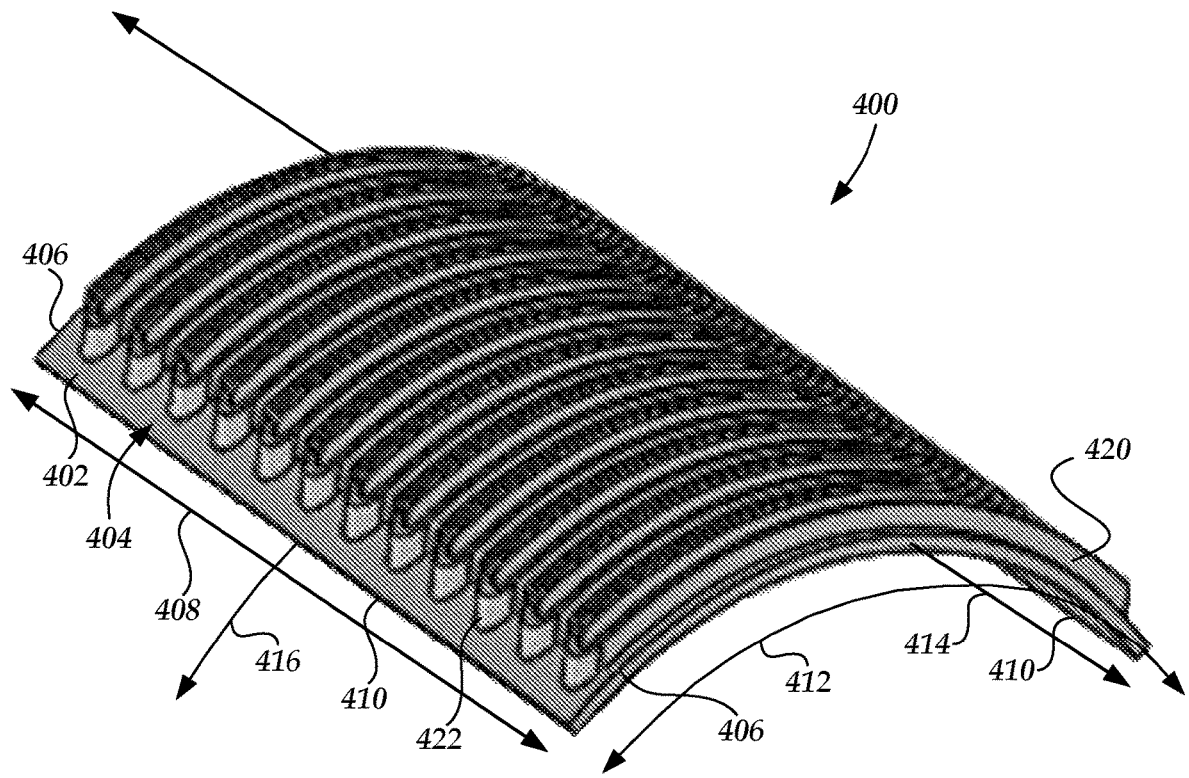
FIG. 4A is a schematic perspective view of one embodiment of an electrical stimulation electrode having a base and at least one finned arrangement that radially extends from the base, according to the invention.

FIG. 4A schematically illustrates one embodiment of an electrical stimulation electrode 400 that includes at least one finned arrangement 404 to increase surface area of the electrode 400. In at least some embodiments, each finned arrangement 404 can have a radiator-like shape. In the illustrated embodiment, the electrode 400 is a segmented electrode, but it will be understood that similar features can be placed on a ring electrode or tip electrode. The electrode 400 includes a base 402 and the at least one finned arrangement 404 extending from the base.

The base 402 defines a perimeter around the base 402 (for example, around each edge of the base 402). In at least some embodiments, each finned arrangement 404 is spaced apart from the perimeter of the base 402. In at least some embodiments, each finned arrangement 404 is spaced apart from an edge of the base 402 by a distance of at least 0.5% of a dimension of the base 402 that is perpendicular to that edge of the base 402. For example, in the illustrated embodiment, each finned arrangement 404 is spaced apart from each widthwise edge 406 of the base 402 by a distance 432 (FIGS. 4B and 5B) of at least 0.5%, 1%, 2%, 5% or more of the length 408 of the base 402 (for example, spaced apart from each widthwise edge 406 of the base 402 by a distance 432 of at least 0.0025 inches or about 0.0063 mm). As another example, in the illustrated embodiment, each finned arrangement 404 is spaced apart from each lengthwise edge 410 of the base 402 by a distance 442 (FIGS. 4B and 5B) of at least two percent of the width 412 of the base 402 (for example, spaced apart from each lengthwise edge 410 of the base 402 by a distance 442 of at least 0.001 inches or about 0.025 mm).

Each finned arrangement 404 radially extends from the base 402. In at least some embodiments, each portion of each finned arrangement 404 radially extends from the base 402 in a direction that is orthogonal to the base 402 (for example, orthogonal to the portion of the base 402 on which that portion of the finned arrangement 404 is disposed). In at least some embodiments, each finned arrangement 404 has a height (for example, a minimum or average height) of at least 0.0005, 0.001, 0.0015, 0.002, or 0.0025 inches (about 0.013, 0.025, 0.038, 0.051, or 0.063 mm, respectively). In at least some embodiments, each portion of each finned arrangement 404 has a height (for example, a maximum height or average height) of no more than 0.00075, 0.0012, 0.0017, 0.0022, or 0.0027 inches (about 0.019, 0.032, 0.044, 0.057, or 0.070 mm, respectively). The height may also be referred to as an elevation.

In at least some embodiments, the electrode 400 includes multiple finned arrangements that are spaced apart from each other along an axis of the base 402. For example, the axis of the base 402 can be a central lengthwise axis 414 of the base 402 (for example, a longitudinal axis along a center length of the base 402), a central widthwise axis 416 of the base 402 (for example, a longitudinal axis along a center width of the base 402) or a diagonal axis of the base 402 (for example, a diagonal longitudinal axis that is offset from both the central widthwise axis 416 and the central lengthwise axis 414 and passes through a point where the central widthwise axis 416 and the central lengthwise axis 414 intersect each other). In at least some embodiments, the electrode 400 includes at least two, three, four, five, six, eight, 10, 12, 16, 20, or more finned arrangements 404. For example, in another embodiment illustrated in FIGS. 5A-5C, the electrode 400 may include only a single finned arrangement 404.

In at least some embodiments, the finned arrangements 404 are spaced apart from each other by a distance that is at most 0.3, 0.5, 1, 1.5, or 2 times the height of the finned arrangements 404. Where there are three or more finned arrangements 404, the finned arrangements 404 can be spaced apart from each other in a uniform or non-uniform arrangement or any combination thereof. For example, two of the finned arrangements 404 can be disposed on opposite sides of an intermediate finned arrangement 404, spaced apart from the intermediate arrangement 404 by two different distances.

Figure 4B:
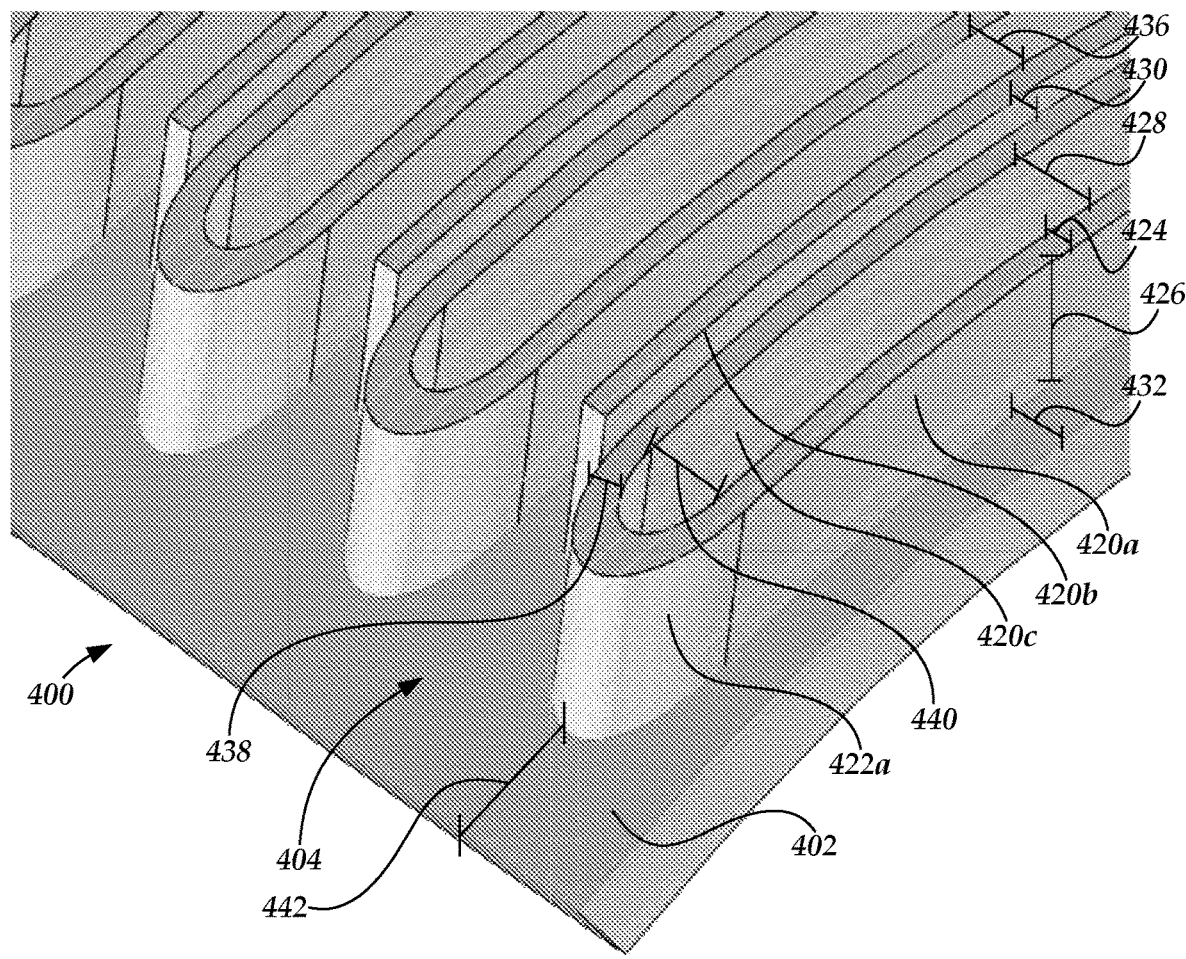
FIG. 4B is a close-up schematic perspective view of a portion of the electrical stimulation electrode of FIG. 4A, according to the invention.

Each finned arrangement 404 includes multiple elongated segments 420 and multiple curved segments 422. Each elongated segment 420 has a length that is substantially greater than the width 424 (for example, as shown in FIG. 4B) of the elongated segment 420 (for example, the length of the elongated segment 420 can be at least 5, 10, 20, 40, 60, 80, or 100 times greater than the width of the elongated segment 420). In at least some embodiments, each of the elongated segments 420 has a height 426 (for example, shown in FIG. 4B as measured straight up from the base 402) that is at least two, three, four, or five times greater than the width of the elongated segment 420 (for example, a maximum width, an average width, or a minimum width). In at least some embodiments, each elongated segment 420 extends along at least 50%, 75%, or 90% of a dimension of the base 402 (for example, the length 408 of the base 402, the width 412 of the base 402, or a diagonal dimension of the base 402 along which the elongated segment 420 extends). For example, in the illustrated embodiment, each elongated segment 420 extends along at least 70% of the width 412 of the base 402.

Each elongated segment 420 has a first end portion and a second end portion. In at least some embodiments, each elongated segment 420 is disposed with the first end portion on a first half of the segmented electrode 400 and the second end portion on a second half of the segmented electrode 400. For example, the first half and the second half can be defined by a central lengthwise axis of the electrode (for example, the central lengthwise axis 414 of the base 402). Alternatively, the first half and the second half can be defined by a central widthwise axis of the electrode (for example, the central widthwise axis 416 of the base 402) or can be defined by a diagonal axis that is offset from both the central widthwise axis and the central lengthwise axis (for example, the diagonal axis of the base 402).

Figure 5A:
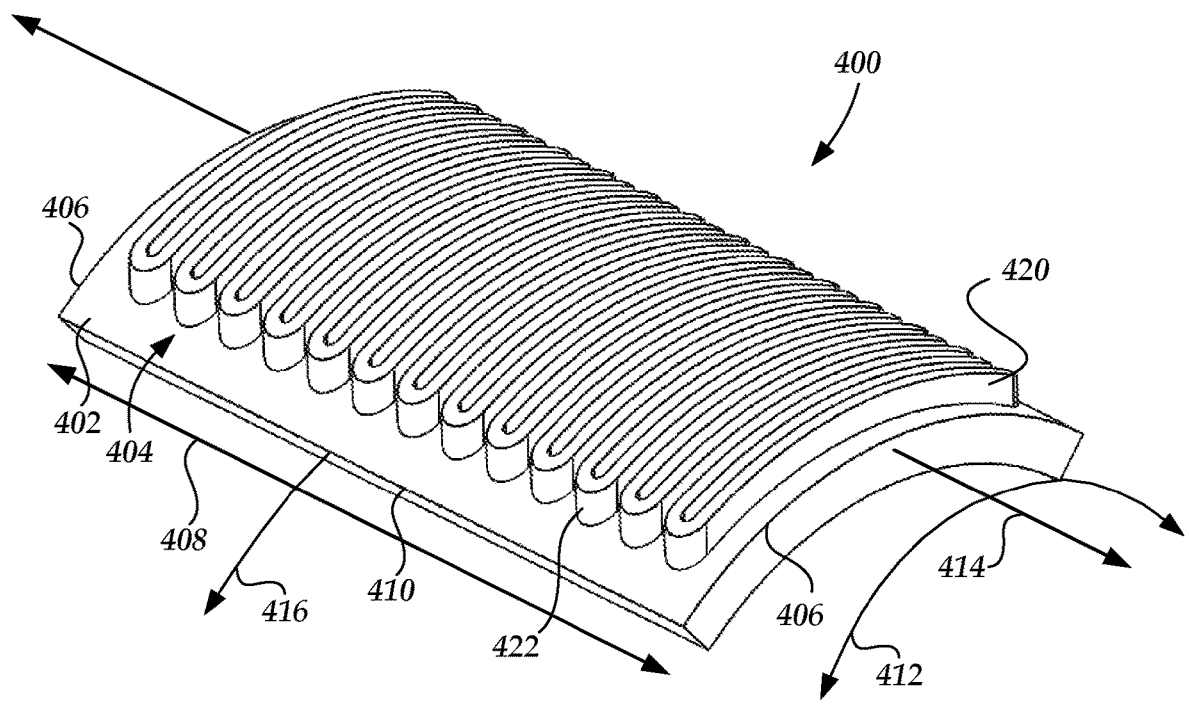
FIG. 5A is a schematic perspective view of another embodiment of the electrical stimulation electrode having the base and at least one finned arrangement that radially extends from the base, according to the invention.
Figure 5B:
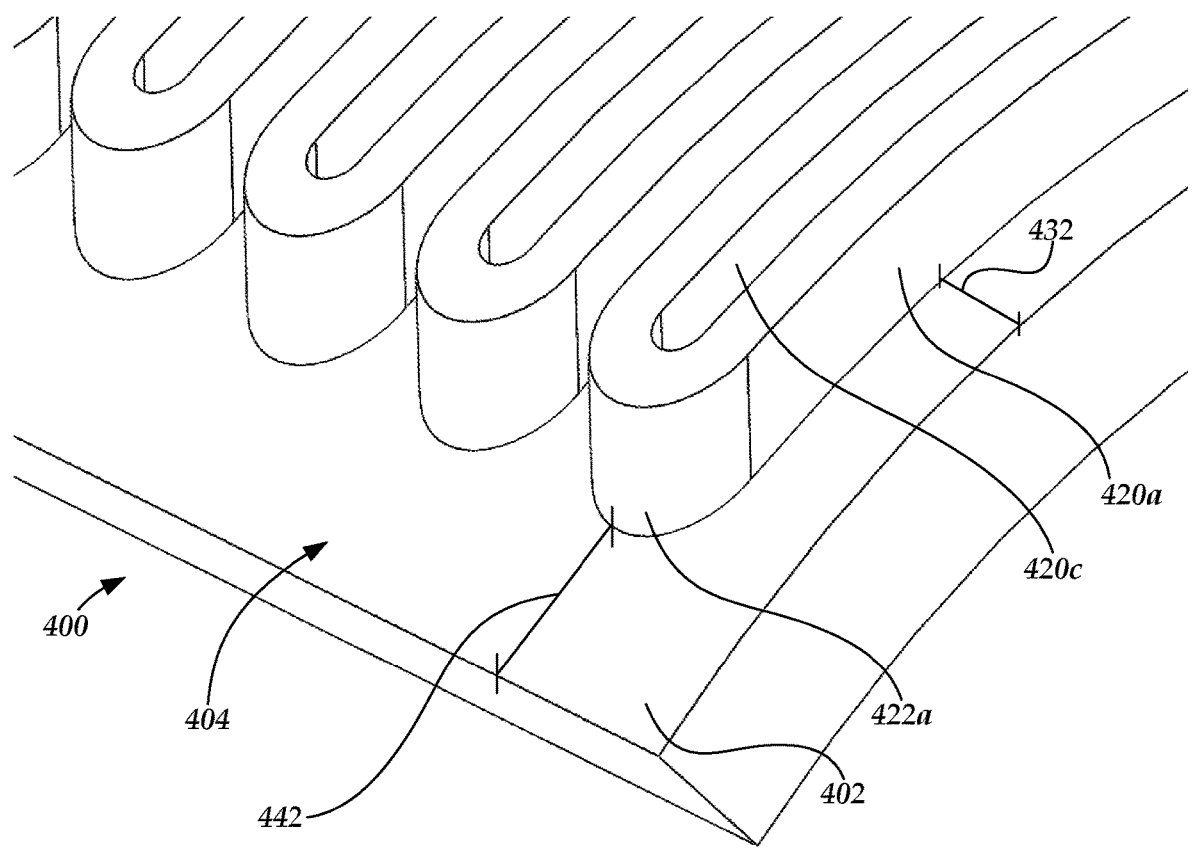
FIG. 5B is a close-up schematic perspective view of a portion of the electrical stimulation electrode of FIG. 5A, according to the invention.
Figure 5C:
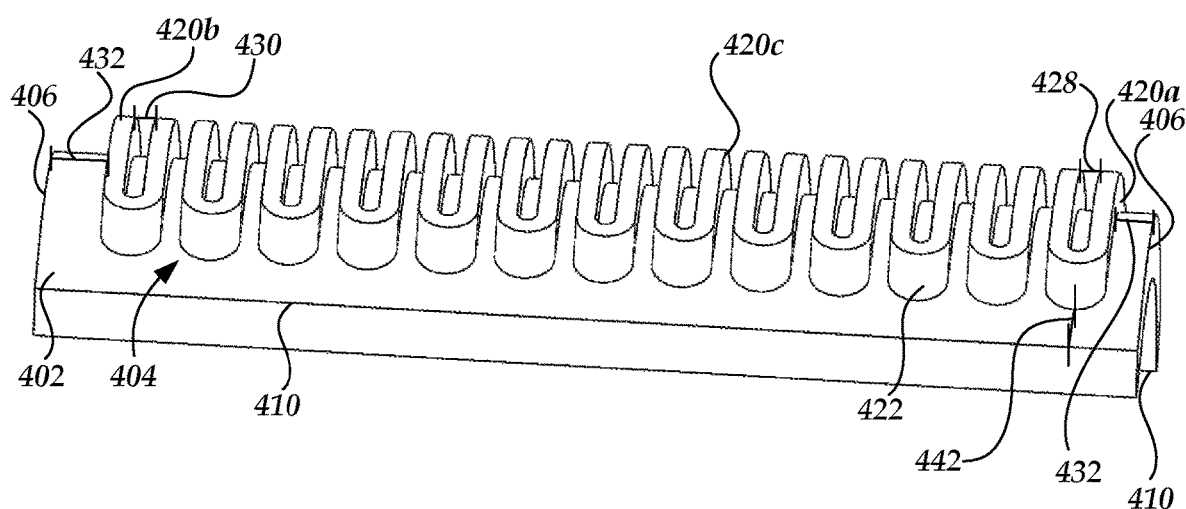
FIG. 5C is a schematic side view of the electrical stimulation electrode of FIG. 5A, according to the invention.

FIG. 4B is a close-up view of a portion of the segmented electrode 400. In at least some embodiments, the finned arrangement 404 includes a first elongated segment 420a, a second elongated segment 420b, and at least one intermediate elongated segment 420c. In the illustrated embodiment, there is only one intermediate elongated segment 420c. The intermediate elongated segment 420c is disposed between the first and second elongated segments 420a, 420b. In another embodiment, as shown in FIGS. 5A-5C, the electrode 400 includes only a single finned arrangement 404 with at least 3, 6, 12, 15, 18, 21, 24, or 27 intermediate elongated segments 420c. In other embodiments, the electrode 400 includes multiple finned arrangements 404 with 1, 2, 3, 3, 6, 12, or more intermediate elongated segments 420c.

In at least some embodiments, all of the elongated segments 420 are parallel to each other (or substantially parallel to each other, as defined by, for example, a margin of error of a process employed to form the elongated segments 420 or a process employed to attach the elongated segments 420 to the base 402, such as, for example, a deviation from parallel of no more than 5°, 10°, 15°, 20°, 25°, 30°, or 35°). In other embodiments, at least two of the elongated segments 420 are not parallel to each other.

The elongated segments 420 are spaced apart from each other along an axis of the base 402 (for example, the central lengthwise axis 414 of the base 402, the central widthwise axis 416 of the base 402, or the diagonal axis of the base 402). Each elongated segment 420 is adjacent (for example, neighboring or nearest on one side) at least one other elongated segment 420. In the illustrated example, the first elongated segment 420a is adjacent to the intermediate elongated segment 420c, and the intermediate elongated segment 420c is adjacent to the second elongated segment 420b.

Each elongated segment 420 is arranged with a distance between the elongated segment 420 and an adjacent elongated segment 420. For example, the distance can be at least 0.25, 0.5, 1, 2, 3, 4, or more times the height of the elongated segment 420. The distance between adjacent elongated segments 420 may be uniform or non-uniform and may be the same or different from the distance between finned arrangements 404. In at least some embodiments, the intermediate elongated segment 420c is arranged with a first distance 428 between the intermediate elongated segment 420c and the first elongated segment 420a and a second distance 430 between the intermediate elongated segment 420c and the second elongated segment 420b, the first distance 428 being at least one, two, three, four, or five times greater than the second distance 430.

Each finned arrangement 404 includes multiple curved segments 422 (only a first curved segment 422a is shown for the finned arrangement 404). In at least some embodiments, each curved segment 422 connects two elongated segments. In at least some embodiments, the connected elongated segments are adjacent to each other. In at least some embodiments, each curved segment 422 can have a height that is the same as or similar to the height of the elongated segments 420 that the curved segment 422 connects. In at least some embodiments, each curved segment 422 can have a thickness 438 (for example, a maximum thickness, average thickness, or maximum thickness) that is the same as or similar to the width of the elongated segments 420 that the curved segment 422 connects. In at least some embodiments, each curved segment 422 can have a width 440 that matches (or substantially matches, as defined by, for example, a margin of error of a process employed to form at least one of the elongated segments 420 or the curved segment 422 or a process employed to attach at least one of the elongated segments 420 or the curved segment 422 to the base 402, such as, for example, a difference in widths of no more than 10%, 20%, 30%, 40%, 50%, 100%, 150%, or 200%) a distance between the elongated segments 420 that the curved segment 422 connects.

In at least some embodiments, each curved segment 422 connects one of the first end portion or the second end portion of one elongated segment 420 to the same one of the first end portion or the second end portion of another elongated segment 420. For example, the first curved segment 422*a* connects the first end portion of the first elongated segment 420*a* to the first end portion of the intermediate elongated segment 420*c* while a second curved segment (not shown in FIG. 4B) connects the second end portion of the intermediate elongated segment 420*c* to the second end portion of the second elongated segment 420*b*.

In at least some embodiments, each of the first and second end portions of each elongated segment 420 directly connects to no more than one curved segment 422. For example, in the illustrated embodiments, a total number of the curved segments 422 in each finned arrangement 404 equals one less than a total number of the elongated segments 420 in the finned arrangement 404.

Each curved segment 422 defines a turn that follows a path from an end portion of one elongated segment 420, through an apex of the curved segment 422, to an end portion of another elongated segment 422. For example, in the illustrated embodiments, the first curved segment 422*a* defines a turn of 180° (from the first end portion of the first elongated segment 420*a* to the first end portion of the intermediate elongated segment 420*c*. In at least some embodiments, each curved segment 422 defines a turn of at least 120°, 135°, 150°, 165°, or 180°.

Each finned arrangement 404 and the base 402 can include the same or different materials.

The segmented electrode 400 can be made by any suitable method including forming the finned arrangement(s) 404 radially extending from the base 402. In at least some embodiments, the finned arrangement(s) 404 are formed using microfabrication processes. For example, a finned arrangement 404 can be formed by building up the finned arrangement 404 on the base 402 using a chemical or physical process (e.g., electrodepositing, sputtering, epitaxy, electrophoretic deposition, or the like). As another example, a finned arrangement 404 can be formed on the base 402 by removing a portion of the base 402 or a portion of a layer deposited on the base 402 using an etching or ablation technique or other photolithographic technique.

In at least some embodiments, the finned arrangement 404 can be formed on the base 402 by other methods including, but not limited to thin-film adhesion (for example, sputtering at least one conductive adhesive that secures the finned arrangement 404 to the base 402), micro-soldering, micromachining (for example, bulk micromachining or surface micromachining), microforming (for example, microstamping, microextrusion, or microcutting), wire bonding (for example, at least one of diffusion bonding, ball bonding, wedge bonding, thermosonic bonding, thermocompression bonding, or ultrasonic bonding), or the like.

In at least some embodiments, each finned arrangement 404 has a thermal conductivity that is the same as or different than a thermal conductivity of the base 402. For example, each finned arrangement 404 can be more conductive than the base 402. As another example, each finned arrangement 404 can be less conductive than the base 402.

In at least some embodiments, the inclusion of at least one finned arrangement 404 on an electrode can reduce the current density for a given amount of current. It is believed that high current density may damage the surrounding tissue (for example, due to excessive tissue heating), thereby reducing susceptibly of the surrounding tissue to stimulation via the stimulation electrodes. In particular, current induced during MRI procedures may cause tissue damage. Using the electrode 400 may reduce or prevent such tissue damage. The finned arrangement(s) 404 increase a surface area of the segmented electrode 400 (at least in comparison to an electrode with the same base 402 but no finned arrangement 404. The increased surface area can be at least 25%, 50%, 75%, 100%, 150%, 200%, 250%, 300%, 350%, or 400% larger than a surface area of the base 402 without the finned arrangement(s) 404. The presence of finned arrangement 404 may also improve anchoring of a lead by promoting ingrowth of tissue that surrounds the electrode 400.

The illustrated electrode 400 is a segmented electrode, but it will be understood that one or more finned arrangements 404 can be disposed on ring electrodes or tip electrodes.

Figure 6:
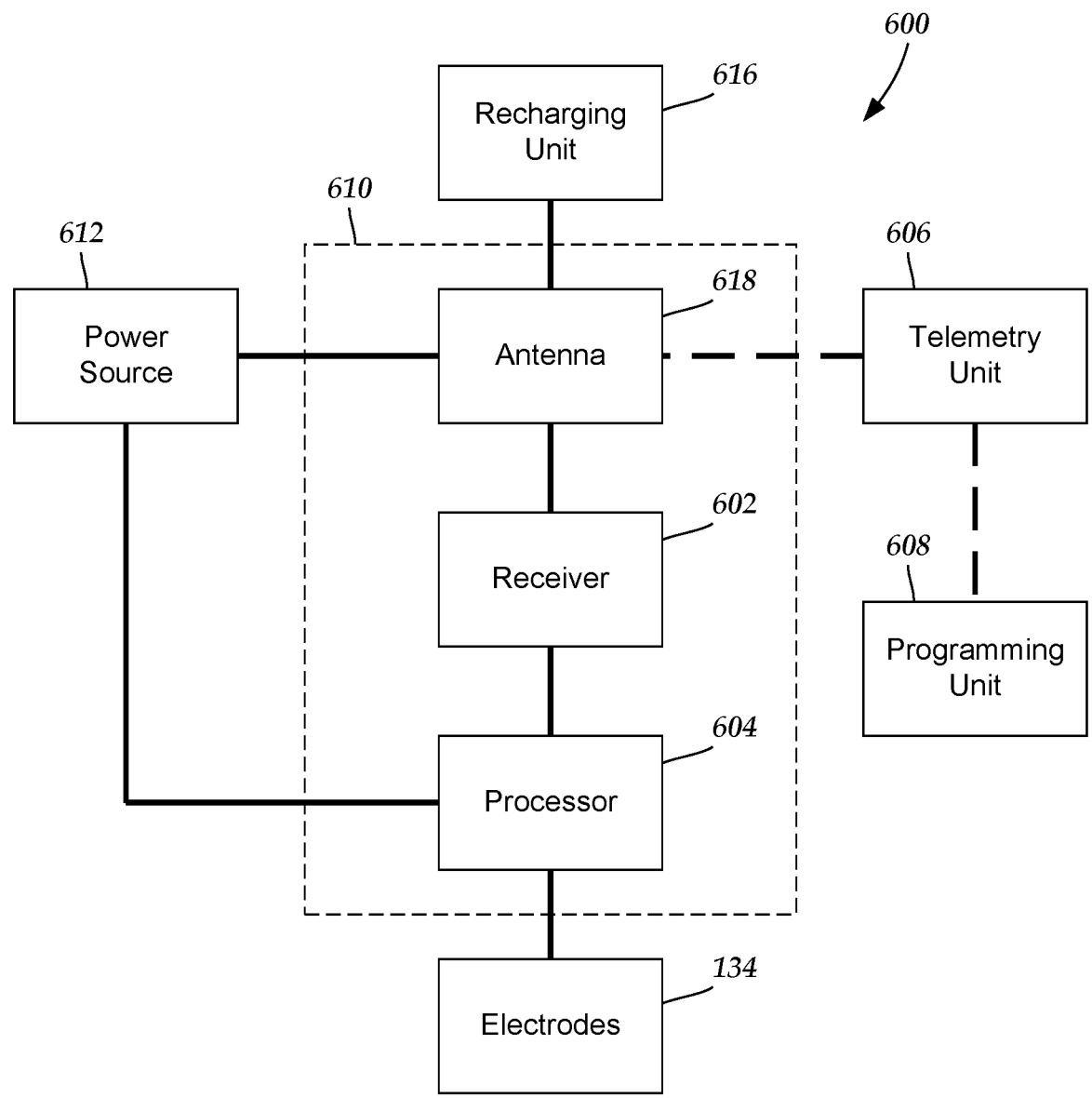
FIG. 6 is a schematic overview of some embodiments of components of an electrical stimulation system, according to the invention.

FIG. 6 is a schematic overview of some embodiments of components of an electrical stimulation system 600 including an electronic subassembly 610 disposed within a control module. It will be understood that the electrical stimulation system 600 can include more, fewer, or different components and can have a variety of different configurations including those configurations disclosed in the stimulator references cited herein.

Some of the components (for example, power source 612, antenna 618, receiver 602, and processor 604) of the electrical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. patent Ser. No. 10/437,193, incorporated herein by reference.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna 618 to a recharging unit 616 external to the user. Examples of such arrangements can be found in the references identified above.

In some embodiments, electrical current is emitted by the electrodes 134 on a lead body to stimulate nerve fibers, muscle fibers, or other body tissues near the electrical stimulation system 600. A processor 604 is generally included to control the timing and electrical characteristics of the electrical stimulation system 600. For example, the processor 604 can, if desired, control one or more of the timing, frequency, amplitude, width, and waveform of the pulses. In addition, the processor 604 can select which electrodes 134 can be used to provide stimulation, if desired. In some embodiments, the processor 604 may select which electrode(s) 134 are cathodes and which electrode(s) 134 are anodes. In some embodiments, the processor 604 may be used to identify which electrodes 134 provide the most useful stimulation of the desired tissue.

Any processor can be used and can be as simple as an electronic device that, for example, produces pulses at a regular interval or the processor 604 can be capable of receiving and interpreting instructions from an external programming unit 608 that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes 134, if desired.

In some embodiments, the antenna 618 is capable of receiving signals (for example, RF signals) from an external telemetry unit 606 which is programmed by a programming unit 608. The programming unit 608 can be external to, or part of, the telemetry unit 606. The telemetry unit 606 can be a device that is worn on the skin of the user or can be carried by the user and can have a form similar to a pager, cellular phone, or remote control, if desired. As another alternative, the telemetry unit 606 may not be worn or carried by the user but may only be available at a home station or at a clinician's office. The programming unit 608 can be any unit that can provide information to the telemetry unit 606 for transmission to the electrical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and receiver 602 can be used to modify or otherwise direct the operation of the electrical stimulation system 600. For example, the signals may be used to modify the pulses of the electrical stimulation system 600 such as modifying one or more of pulse width, pulse frequency, pulse waveform, and pulse amplitude. The signals may also direct the electrical stimulation system 600 to cease operation, to start operation, to start charging the battery, or to stop charging the battery. In other embodiments, the stimulation system 600 does not include an antenna 618 or receiver 602 and the processor 604 operates as programmed.

Optionally, the electrical stimulation system 600 may include a transmitter (not shown) coupled to the processor 604 and the antenna 618 for transmitting signals back to the telemetry unit 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

The above specification and examples provide a description of the arrangement and use of the invention. Since many embodiments of the invention can be made without departing from the spirit and scope of the invention, the invention also resides in the claims hereinafter appended.

What is claimed as new and desired to be protected by Letters Patent of the United States is:

1. A stimulation lead, comprising:
   a lead body comprising a longitudinal surface, a distal end portion, a proximal end portion, and a longitudinal length;
   a plurality of terminals disposed along the proximal end portion of the lead body;
   a plurality of electrodes disposed along the distal end portion of the lead body, the plurality of electrodes comprising a plurality of segmented electrodes, each of the segmented electrodes comprising a base and at least one finned arrangement radially extending from the base, wherein the base comprises a perimeter around the base and the at least one finned arrangement is spaced apart from the perimeter, each of the at least one finned arrangement comprising:
   a plurality of elongated segments comprising a first elongated segment, a second elongated segment, and at least one intermediate elongated segment disposed between the first and second elongated segments, each of the elongated segments extending along at least 50% of a length of a dimension of the base and having a first end portion and a second end portion; and
   a plurality of curved segments comprising a first curved segment and a second curved segment, wherein the first curved segment connects the first end portion of the first elongated segment to the first end portion of one of the at least one intermediate elongated segment that is adjacent to the first elongated segment and the second curved segment connects the second end portion of the second elongated segment to the second end portion of at least one of the at least one intermediate elongated segment that is adjacent to the second elongated segment; and
   a plurality of conductors electrically coupling the terminals to the electrodes.

2. The stimulation lead of claim 1, wherein each of the elongated segments extends along at least 75% of the length of the dimension of the base.

3. The stimulation lead of claim 1, wherein each of the curved segments defines a turn of at least 150°.

4. The stimulation lead of claim 1, wherein all of the elongated segments are parallel to each other.

5. The stimulation lead of claim 1, wherein the at least one finned arrangement comprises multiple finned arrangements that are spaced apart from each other along an axis of the base.

6. The stimulation lead of claim 1, wherein the at least one intermediate elongated segment comprises a single intermediate elongated segment.

7. The stimulation lead of claim 1, wherein the at least one intermediate elongated segment comprises at least two intermediate segments connected together using at least one of the curved segments.

8. The stimulation lead of claim 1, wherein the at least one finned arrangement comprises a single finned arrangement with at least 15 intermediate elongated segments.

9. The stimulation lead of claim 1, wherein each of the elongated segments has a height of at least 0.0005 inches.

10. The stimulation lead of claim 1, wherein each of the elongated segments has a height of at least 0.0015 inches.

11. The stimulation lead of claim 1, wherein the elongated segments are arranged such that a distance between one elongated segment and another elongated segment adjacent to the one elongated segment is no more than a height of the one elongated segment.

12. The stimulation lead of claim 1, wherein each of the segmented electrodes has a first half and a second half, and each of the elongated segments of the at least one finned arrangement of the segmented electrode are disposed with the first end portions on the first half of the segmented electrode and with the second end portions on the second half of the segmented electrode.

13. An electrical stimulation system, comprising:
the stimulation lead of claim 1; and
a control module coupleable to the stimulation lead, the control module comprising:
a housing; and
an electronic subassembly disposed in the housing.

14. A segmented stimulation electrode, comprising:
a base comprising a perimeter around the base; and
at least one finned arrangement radially extending from the base, wherein the at least one finned arrangement is spaced apart from the perimeter, each of the at least one finned arrangement comprising:
a plurality of elongated segments comprising a first elongated segment, a second elongated segment, and at least one intermediate elongated segment disposed between the first and second elongated segments, each of the elongated segments extending along at least 50% of a length of a dimension of the base and having a first end portion and a second end portion; and
a plurality of curved segments comprising a first curved segment and a second curved segment, wherein the first curved segment connects the first end portion of the first elongated segment to the first end portion of one of the at least one intermediate elongated segment that is adjacent to the first elongated segment and the second curved segment connects the second end portion of the second elongated segment to the second end portion of at least one of the at least one intermediate elongated segment that is adjacent to the second elongated segment.

15. The segmented stimulation electrode of claim 14, wherein each of the elongated segments extends along at least 75% of the length of the dimension of the base.

16. The segmented stimulation electrode of claim 15, wherein each of the curved segments defines a turn of at least 150°.

17. The segmented stimulation electrode of claim 16, wherein the at least one intermediate elongated segment comprises a single intermediate elongated segment.

18. A method of making a segmented stimulation electrode, the method comprising:
providing a base comprising a perimeter around the base; and
forming at least one finned arrangement radially extending from the base, wherein the at least one finned arrangement is spaced apart from the perimeter, each of the at least one finned arrangement comprising:
a plurality of elongated segments comprising a first elongated segment, a second elongated segment, and at least one intermediate elongated segment disposed between the first and second elongated segments, each of the elongated segments extending along at least 50% of a length of a dimension of the base and having a first end portion and a second end portion; and
a plurality of curved segments comprising a first curved segment and a second curved segment, wherein the first curved segment connects the first end portion of the first elongated segment to the first end portion of one of the at least one intermediate elongated segment that is adjacent to the first elongated segment and the second curved segment connects the second end portion of the second elongated segment to the second end portion of at least one of the at least one intermediate elongated segment that is adjacent to the second elongated segment.

19. The method of claim 18, wherein forming the at least one finned arrangement comprises building at least one portion of the at least one finned arrangement up from the base.

20. The method of claim 18, wherein forming the at least one finned arrangement comprises removing at least one portion of the base.

* * * * *